United States Patent [19]
Sudilovsky et al.

[11] Patent Number: 5,089,502
[45] Date of Patent: Feb. 18, 1992

[54] METHOD FOR PREVENTING OR TREATING ANXIETY EMPLOYING A CALCIUM CHANNEL BLOCKER

[75] Inventors: Abraham Sudilovsky, Lawrenceville; Zola P. Horovitz, Princeton, both of N.J.

[73] Assignee: E. R. Squibb & Sons, Inc., Princeton, N.J.

[21] Appl. No.: 564,937

[22] Filed: Aug. 9, 1990

Related U.S. Application Data

[63] Continuation of Ser. No. 360,955, Jun. 2, 1989, abandoned.

[51] Int. Cl.⁵ .................. A61K 31/55; A61K 31/54; A61K 31/535; A61K 31/505
[52] U.S. Cl. .................. 514/274; 514/211; 514/212; 514/227.8; 514/235.8; 514/252; 514/354; 514/356; 514/523
[58] Field of Search .............. 514/211, 274, 354, 523, 514/212, 227.8, 235.8, 252

[56] References Cited

U.S. PATENT DOCUMENTS

| | | | |
|---|---|---|---|
| 3,562,257 | 2/1971 | Kugita et al. | 540/491 |
| 4,855,301 | 8/1989 | Atwal | 514/269 |
| 4,931,430 | 6/1990 | Sudilovsky et al. | 514/91 |

FOREIGN PATENT DOCUMENTS

0218996A2  4/1987  European Pat. Off.
0321221A2  6/1989  European Pat. Off.

*Primary Examiner*—Cecilia Shen
*Attorney, Agent, or Firm*—Burton Rodney

[57] ABSTRACT

A method is provided for inhibiting onset of or treating anxiety by administering a calcium channel blocker such as diltiazem or nifedipine, over a prolonged period of treatment.

20 Claims, 4 Drawing Sheets

METHOD FOR PREVENTING OR TREATING ANXIETY EMPLOYING A CALCIUM CHANNEL BLOCKER

This is a continuation of application Ser. No. 360,955, filed June 2, 1989, now abandoned.

FIELD OF THE INVENTION

The present invention relates to a method for preventing or treating anxiety including chronic and acute anxiety disorders in mammalian species by administering a calcium channel blocker, such as diltiazem, nifedipine or verapamil.

BACKGROUND OF THE INVENTION

Sudilovsky et al, "Captopril Delays Extinction of Conditional Aviodance Response in the Rat," Poster Presentation, 14th Congress of the Collegium Internationale Neuro-Psychopharmacologicum, Florence, Italy, June, 1984, disclose that after 10 days methyldopa was found to impair conditioned avoidance acquisition in the rat and to accelerate conditioned avoidance extinction, whereas captopril did not affect conditioned avoidance acquisition and significantly delayed conditioned avoidance extinction.

Katz, A. M. et al., "Differential effects of 1,4-dihydropyridine calcium channel blockers," J. Clin. Pharmacol (US), Nov. 1987, 27 (11) 825–34, disclose that selectivity for the cerebrovascular bed makes nimodipine potentially useful in the treatment of dementia.

Albizzati, M.G., et al., "Cyclandelate versus Flunarizine, a double-blind study in a selected group of patients with dementia," Drugs 1987, 33 Suppl. 2, 90–6, disclose that when flunarizine was tested in patients with dementia, improvement was observed in neurological impairment, ischemia scores, Gottfries scale and Hamilton depression scores.

Qin, W. C., et al., in Chung Kuo I Hsueh Ko Hsueh Yuan Hsueh Pao, Oct. 1986, 8(5), 366–70, disclose that nimodipine, nifedipine and vincamine improve amnesia induced by anisodine and sodium nitrite in rats and mice.

U.S. Pat. No. 4,386,095 discloses that certain diaminopyridines improve cognition.

U.S. Pat. No. 4,694,085 discloses that 5,6-dihydropyrrolo(2,1-a)isoquinolines are calcium antagonists and nootropic agents.

UK patent application No. 2,176,788A discloses that certain 2-halonicergoline compounds are calcium antagonists and improve cognitive action of the brain.

DESCRIPTION OF THE INVENTION

In accordance with the present invention, a method is provided for preventing or treating anxiety in mammalian species over a prolonged period wherein a therapeutically effective amount of a calcium channel blocker is systemically, such as orally or parenterally, or transdermally administered over a prolonged period, to prevent or treat anxiety during such period.

The method of the invention is useful in treating or preventing anxiety including chronic and acute anxiety disorders (or anxiety and phobic neuroses) including panic disorder with or without agoraphobia, agoraphobia, social phobia, simple phobia, obsessive compulsive disorder (or obsessive compulsive neurosis), post-traumatic stress disorder, generalized anxiety disorder, anxiety disorder not otherwise specified, and mixed anxiety-depression.

In addition, the method of the invention is useful in treating or preventing anxiety associated with withdrawal from drugs of dependency and/or addiction. Thus, the method of the invention is useful in reducing anxiety and thus facilitate withdrawal from alcohol dependency, nicotine dependency, cocaine dependency and benzodiazepine dependency as well as withdrawal from other drug dependency.

The calcium channel blocker also referred to as calcium entry blocker or calcium antagonist which is used herein is preferably diltiazem which is disclosed in U.S. Pat. No. 3,562,257 and which has the chemical name 3-(acetyloxy)-5-[2-(dimethylamino) ethyl-2-3-dihydro-2-(4-methoxyphenyl)-1,5-benzothiazepin-4(5H)-one and the structure In addition, the calcium channel blocker may be a benzazepine derivative such as disclosed in U.S. Pat. No. 4,748,239 and which has the formula pos or a pharmaceutically acceptable salt thereof wherein $R_1$ is hydrogen, alkyl, alkanoyl, alkenyl, arylcarbonyl, heteroarylcarbonyl or $R_2$ and $R_3$ are each independently hydrogen, alkyl, cycloalkyl or arylalkyl or $R_2$ and $R_3$ together with the nitrogen atom to which they are attached are pyrrolidinyl, piperidinyl, or morpholinyl;

$R_4$ and $R_5$ are each independently hydrogen, halogen, alkyl, alkoxy, aryloxy, arylalkoxy, diarylalkoxy, arylalkyl, cyano, hydroxy, alkanoyloxy, fluoro substituted alkoxy, fluoro substituted alkyl, (cycloalkyl)alkoxy, —NO$_2$, —NX$_3$X$_4$, —S(O)$_m$alkyl, —S(O)$_m$aryl, n is 2 or 3;

m is 0, 1 or 2;

X$_1$ and X$_2$ are each independently hydrogen, alkyl, aryl or heteroaryl, or X$_1$ and X$_2$ together with the nitrogen atom to which they are attached are pyrrolidinyl, piperidinyl or morpholinyl;

X$_3$ and X$_4$ are each independently hydrogen, alkyl, alkanoyl, arylcarbonyl, heteroarylcarbonyl, or

X$_5$ is hydroxy, alkoxy, aryloxy, amino, alkylamino or dialkylamino; and X$_6$ is alkyl, alkoxy or aryloxy; with the proviso that if R$_4$ is a 7-alkyl group, it must have a tertiary carbon atom bonded to the ring;

wherein the term "aryl" refers to phenyl and phenyl substituted with 1, 2 or 3 amino, alkylamino, dialkylamino, nitro, halogen, hydroxyl, trifluoromethyl, alkyl of 1 to 4 carbon atoms, alkoxy of 1 to 4 carbon atoms, alkanoyloxy, carbamoyl, or carboxyl groups; and the term "heteroaryl" refers to pyridinyl, pyrrolyl, imidazolyl, furyl, thienyl, or thiazolyl.

A preferred such benzazepine derivative has the structure wherein R$_2$ and R$_3$ are each CH3 or one of R$_2$ and R$_3$ is H and the other is CH3, including the hydrochloride salts thereof.

Another class of benzazepine derivatives suitable for use here has the formula and the pharmaceutically acceptable salts thereof, wherein

R$_3$ and R$_4$ are each independently hydrogen, halogen, alkyl, alkoxy, aryloxy, arylalkoxy, diarylalkoxy, arylalkyl, cyano, hydroxy, alkanoyloxy, fluoro substituted alkoxy, fluoro substituted alkyl, (cycloalkyl)alkoxy, —NO$_2$, —NY$_{10}$Y$_{11}$, —S(O)$_m$alkyl, —S(O)$_m$aryl, or n is 0, 1, 2 or 3;
m is 0, 1 or 2;
$Y_1$ and $Y_2$ are each hydrogen or alkyl, $Y_1$ is hydrogen and $Y_2$ is alkenyl, alkynyl, aryl, heteroaryl, or cycloalkyl, or $Y_1$ and $Y_2$ together with the carbon atom to which they are attached are cycloalkyl;
$Y_3$ is hydrogen, alkyl, alkanoyl, alkenyl, arylcarbonyl, heteroarylcarbonyl, or $Y_4$ and $Y_5$ are each independently hydrogen, alkyl, aryl or arylalkyl, provided that when both are present they are not both hydrogen, and provided further that when both are attached to the same carbon atom neither of them is hydrogen;
$Y_6$ and $Y_7$ are each independently hydrogen, alkyl, cycloalkyl or arylalkyl or $Y_6$ and $Y_7$ together with the nitrogen atom to which they are attached are azetidinyl, pyrrolidinyl, piperidinyl, or morpholinyl;
$Y_8$ and $Y_9$ are each independently hydrogen, alkyl, aryl or heteroaryl, or $Y_8$ and $Y_9$ together with the nitrogen atom to which they are attached are pyrolidinyl, piperidinyl or morpholinyl;
$Y_{10}$ and $Y_{11}$ are each independently hydrogen, alkyl, alkanoyl, arylcarbonyl, heteroarylcarbonyl, or $Y_{12}$ is hydroxy, alkoxy, aryloxy, amino, alkylamino or dialkylamino; and
$Y_{13}$ is alkyl, alkoxy or aryloxy.

These compounds are disclosed in U.S. application Ser. No. 208,521, filed June 20, 1988, now abandoned.

Preferred such benzazepines are [3R-[1(S*),3α, 4α]]-3-(acetyloxy)-1,3,4,5-tetrahydro-4-(4-methoxyphenyl)-1-(2-( pyrrolidinylmethyl)-6-(trifluoromethyl)-2H-1-benzazepin-2-one or a pharmaceutically acceptable salt thereof, preferably the monohydrochloride and [3(R)-[1(S*),3α,4α]]-1,3,4,5-tetrahydro-3-hydroxy-4-(4-methoxyphenyl)-1-(2-pyrrolidinylmethyl)-6-( trifluoromethyl)-2H-1-benzazepin-2-one, or a pharmaceutically acceptable salt thereof, preferably the monohydrochloride.

The calcium channel blocker may also be a 2-thioxo-4-methyl-6-substituted phenyl-1,5(2H)-pyrimidinedicarboxylic acid ester having the formula Wherein $R_a$ is 2-(trifluoromethyl)phenyl, 2-chlorophenyl, 2-nitrophenyl, or 3-nitrophenyl and
$R_b$ is phenyl, 2-chlorophenyl, or 4-fluorophenyl, which are disclosed in U.S. application Ser. No. 00,618 filed Jan. 5, 1987; The preferred pyrimidine is the compound (R)-3,6-dihydro-4-methyl-2-thioxo-6-[2-(trifluoromethyl)phenyl]-1,5(2H)-pyrimidinedicarboxylic acid, 1-[1-[(2-chlorophenyl) methyl]-4-piperidinyl]-5-(1-methylethyl) ester, monohydrochloride, which is prepared using the methodology described in U.S. application Ser. No. 00,618.

Another class of pyrimidine calcium channel blockers suitable for use herein has the formula or a pharmaceutically acceptable salt thereof wherein
X is oxygen or sulfur;
$R_x$ is hydrogen, alkyl, cycloalkyl, aryl, or arylalkyl and $R_c$ is hydrogen, alkyl, cycloalkyl, aryl, or halo substituted alkyl, or $R_x$ and $R_c$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-piperazinyl or 1-pyrrolidinyl, 1-piperidinyl, or 1-azeipinyl substituted with alkyl, alkoxy, alkylthio, halo, trifluoromethyl or hydroxy;
$R_d$ is hydrogen, alkyl, alkenyl, alkynyl, cycloalkyl, aryl, or halo substituted alkyl;
$R_e$ is hydrogen, alkyl, cycloalkyl, aryl, or halo substituted alkyl;
$R_f$ b is 2,1,3-benzoxadiazol-4-yl, phenyl, or phenyl substituted with one, two or three alkyl, halo, nitro, cyano, amino, dialkylamino, trifluoromethyl, isothiocyanato or isocyanato groups;
$R_g$ and $R_h$ are each independently hydrogen, alkyl, —$(CH_2)_{q1}$-aryl or —$(CH_2)_{q1}$-cycloalkyl;
$Y^a$ is cycloalkyl, aryl, hydroxyl, alkoxy, aryl-$(CH_2)_m$—O—, mercapto, alkylthio, aryl-$(CH_2)_m$—S—, amino, substituted amino, carbamoyl, (substituted $$\underset{\text{amino)-C}-}{\overset{\text{O}}{\overset{\|}{\text{C}}}},$$

carboxyl, alkoxycarbonyl, $$\underset{\text{alkyl-C}-}{\overset{\text{O}}{\overset{\|}{\text{C}}}},$$

$$\underset{\text{aryl-(CH}_2)_{m1}-\text{C}-}{\overset{\text{O}}{\overset{\|}{\text{C}}}},\ \underset{\text{alkyl-C}-\text{O}-}{\overset{\text{O}}{\overset{\|}{\text{C}}}}\ \text{or}\ \underset{\text{aryl-(CH}_2)_{m1}-\text{C}-\text{O};}{\overset{\text{O}}{\overset{\|}{\text{C}}}}$$

$Y^b$ is cycloalkyl, aryl, carbamoyl, $$\underset{\text{(substituted amino)-C}-}{\overset{\text{O}}{\overset{\|}{\text{C}}}},$$

carboxyl, alkoxycarbonyl, $$\underset{\text{alkyl-C}-}{\overset{\text{O}}{\overset{\|}{\text{C}}}},\ \text{or}\ \underset{\text{aryl-(CH}_2)_{m1}-\text{C}-;}{\overset{\text{O}}{\overset{\|}{\text{C}}}}$$

$Y^c$ is hydroxyl, alkoxy, aryl—$(CH_2)_{m1}$—O—, mercapto, alkylthio, aryl—$(CH_2)_{m1}$—S—, $$\underset{\text{alkyl-C}-\text{O}-,}{\overset{\text{O}}{\overset{\|}{\text{C}}}}\ \underset{\text{aryl-(CH}_2)_{m1}-\text{C}-\text{O}-,}{\overset{\text{O}}{\overset{\|}{\text{C}}}}$$

amino, or substituted amino;
$q_1$ is 0, 1, 2 or 3;
$m_1$ is 0 or an integer of 1 to 6;
$n_1$ is 0 or an integer of 1 to 5; and
$p_1$ is an integer of 1 to 5; wherein
the term "cycloalkyl" refers to a cycloalkyl group having 3,4,5,6 or 7 carbon atoms;
the term "aryl" refers to phenyl or phenyl substituted with one, two or three alkyl, alkoxy, alkylthio, halo, nitro, cyano, hydroxy, amino, alkylamino, dialkylamino, trifluoromethyl, isothiocyanato, isocyanato, or difluoromethoxy groups;
the term "substitued amino" refers to a group of the formula —$NZ_1Z_2$ wherein $Z_1$ is hydrogen, alkyl, or aryl—$(CH_2)_{m1}$—and $Z_2$ is alkyl or aryl—$(CH_2)_{m1}$—.

Preferred is the compound having the name (R)-1-(aminocarbonyl)-4-(3-chlorophenyl)-1,2,3,4-tetrahydro-6-methyl-2-oxo-5-pyrimidinecarboxylic acid, 1-methylethyl ester.

4-Phenyl-1,4-dihydropyridine calcium antagonists may be employed which will have the structure wherein $R_1$ and $R_2$ may be the same or different and are lower alkyl or lower alkoxy (lower alkyl) where lower alkyl and lower alkoxy contain 1 to 4 carbons.

The above compounds and methods for preparing same are disclosed in U.S. Pat. Nos. 3,644,627, 3,485,847, 3,488,359, 3,574,843, 3,799,934, 3,932,645 and 4,154,839 which are incorporated herein by reference.

The dihydropyridine calcium antagonist present in the composition of the invention will preferably be nifedipine, that is, the compound of formula C wherein $R_1$ is $CH_3$, $R_2$ is $CH_3$ and $NO_2$ is at the 2-position, namely, which is disclosed in U.S. Pat. Nos. 3,644,627 and 3,485,847.

Other preferred 4-phenyl-1,4-dihydropyridine calcium antagonists suitable for use herein include niludipine, that is, the compound of formula C wherein $R_1$ is —$(CH_2)_2OC_3H_7$, $R_2$ is —$(CH_2)_2OC_3H_7$ and $NO_2$ is at the 3-position (disclosed in U.S. Pat. Nos. 3,488,359 and 3,574,843); nimodipine, that is the compound of formula C wherein $R_1$ is —$(CH_2)_2OCH_3$, $R_2$ is —$CH(CH_3)_2$ and $NO_2$ is at the 3-position (disclosed in U.S. Pat. Nos. 3,799,934 and 3,932,645); nitrendipine, that is, the compound of formula C wherein $R_1$ is —$CH_2CH_3$, $R_2$ is —$CH_3$ and $NO_2$ is at the 3-position (disclosed in U.S. Pat. Nos. 3,799,934 and 3,932,645); and nisoldipine, that is, the compound of formula C wherein $R_1$ is —$CH_3$, $R_2$ is —$CH_2CH(CH_3)_2$ and $NO_2$ is at the 2-position (disclosed in U.S. Pat. Nos. 3,799,934, 3,932,645 and 4,154,839.

In addition, verapamil and nicardipine may be employed.

The disclosure of the above-mentioned U.S. patents are incorporated herein by reference.

In carrying out the method of the present invention, calcium channel blocker may be administered to mammalian species, such as monkeys, dogs, cats, rats, humans, etc. and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like. Oral dosage forms are preferred, although parenteral forms are quite satisfactory as well.

The dose administered must be carefully adjusted according to age, weight and condition of the patient, as well as the route of administration, dosage form and regimen and the desired result.

Thus, for oral administration, a satisfactory result may be obtained employing the calcium channel blocker in an amount within the range of from about 0.01 mg/kg to about 100 mg/kg and preferably from about 0.1 mg/kg to about 25 mg/kg.

A preferred oral dosage form, such as tablets or capsules, will contain the calcium channel blocker in an amount of from about 0.1 to about 500 mg, preferably from about 125 to about 200 mg, and more preferably from about 25 to about 150 mg.

For parenteral administration, the calcium channel blocker will be employed in an amount within the range of from about 0.005 mg/kg to about 10 mg/kg and preferably from about 0.01 mg/kg to about 1 mg/kg.

The composition described above may be administered in the dosage forms as described above in single or divided doses of one to four times daily. It may be advisable to start a patient on a low dose and work up gradually to a high dose.

Tablets of various sizes can be prepared, e.g., of about 10 to 700 mg in total weight, containing the active substance in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending the active substance in a conventional liquid vehicle acceptable for pharmaceutical administration so as to provide the desired dosage in one to four teaspoonsful.

Such dosage forms can be administered to the patient on a regimen of one to four doses per day.

In formulating the compositions, the active substance, in the amount described above, is compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

Many of the active substances described above form commonly known, pharmaceutically acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for as long as the potential for onset of anxiety remains or the symptoms continue. Sustained release forms of such formulations which may provide such amounts biweekly, weekly, monthly and the like may also be employed. A dosing period of at least one to two weeks are required to achieve minimal benefit. In addition, transdermal delivery devices may be employed as well.

BRIEF DESCRIPTION OF FIGURES

All of the accompanying Figures are graphs or charts of test data obtained as described in the working Examples.

The following Examples represent preferred embodiments of the present invention.

EXAMPLE 1

A diltiazem formulation suitable for oral administration in preventing or treating anxiety is set out below.

1000 tablets each containing 100 mg of diltiazem were produced from the following ingredients.

| | |
|---|---|
| Diltiazem | 100 g |
| Corn starch | 50 g |
| Gelatin | 7.5 g |
| Avicel (microcrystalline cellulose) | 25 g |
| Magnesium stearate | 2.5 g |

The diltiazem and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 100 mg of active ingredient which is used for treating anxiety.

EXAMPLE 2

1000 tablets each containing 60 mg of SQ 32,324 are produced from the following ingredients:

| | |
|---|---|
| (d-cis)-3-(acetyloxy)-1,3,4,5-tetrahydro-4-(4-methoxyphenyl))-1-[2-(methylamino)ethyl]-6-(trifluoromethyl)-2H-1-benzazepin-2-one, monohydrochloride salt (SQ 32,324) | 60 g |
| Lactose | 100 g |
| Avicel | 150 g |
| Corn starch | 50 g |
| Magnesium stearate | 5 g |

SQ 32,324 lactose and Avicel are admixed, then blended with the corn starch. Magnesium stearate is added. The dry mixture is compressed in a tablet press to form 1000 505 mg tablets each containing 60 mg of active ingredient. The tablets are coated with a solution of Methocel E 15 (methyl cellulose) including as a color a lake containing yellow #6. The resulting tablets are useful in preventing anxiety.

EXAMPLE 3

Two piece #1 gelatin capsules each containing 10 mg of nifedipine are filled with a mixture of the following ingredients:

| | |
|---|---|
| Nifedipine | 10 mg |

| | |
|---|---|
| Magnesium stearate | 7 mg |
| USP lactose | 193 mg |

The resulting capsules are useful in preventing or treating anxiety.

EXAMPLE 4

An injectable solution for use in treating or preventing anxiety is produced as follows:

| | |
|---|---|
| (d-cis)-3-(acetyloxy)-1-[2-dimethyl-amino)ethyl]-1,3,4,5-tetrahydro-4-(4-methoxyphenyl)-6-(trifluoromethyl)-2H-1-benzazepin-2-one, monohydrochloride (SQ 31,765) | 500 mg |
| Methyl paraben | 5 mg |
| Propyl paraben | 1 mg |
| Sodium chloride | 25 g |
| Water for injection qs. | 5 l. |

SQ 31,765, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 0.5 mg of active ingredient per ml of solution for injection.

EXAMPLE 5

1000 tablets each containing 20 mg of the benzazepine derivative SQ 33,351 are produced from the following ingredients:

| | |
|---|---|
| [3R-[1(S*),3a,4a]]-3-(acetyloxy)-1,3,4,5-tetrahydro-4-(4-methoxyphenyl)-1-(2-pyrrolidinylmethyl)-6-(trifluoromethyl)-2H-1-benzazepin-2-one monohydrochloride (SQ 33,351) | 20 g |
| Lactose | 100 g |
| Avicel | 150 g |
| Corn starch | 50 g |
| Magnesium stearate | 5 g |

SQ 33,351, lactose and Avicel are admixed, then blended with the corn starch. Magnesium stearate is added. The dry mixture is compressed in a tablet press to form 1000 505 mg tablets each containing 100 mg of active ingredient. The tablets are coated with a solution of Methocel E 15 1 (methyl cellulose) including as a color a lake containing yellow #6. The resulting tablets are useful in preventing or treating anxiety.

EXAMPLE 6

Two piece #1 gelatin capsules each containing 50 mg of SQ 33,537 are filled with a mixture of the following ingredients:

| | |
|---|---|
| [3(R)-[1(S*),3a,4a]]-1,3,4,5-tetrahydro-3-hydroxy-4-(4-methoxyphenyl)-1-(2-pyrrolidinylmethyl)-6-(trifluoromethyl)-2H-1-benzazepin-2-one, monohydrochloride (SQ 33,537) | 25 mg |
| Magnesium stearate | 7 mg |
| USP lactose | 193 mg |

The resulting capsules are useful in treating or preventing anxiety.

EXAMPLE 7

1000 tablets each containing the following ingredients:

| | |
|---|---|
| (R)-3,6-Dihydro-4-methyl-2-thioxo-6-[2-(trifluoromethyl)phenyl]-1,5(2H)pyrimidinedicarboxylic acid, 1-[1-[(4-fluorophenyl)methyl]-4-piperidinyl]5-(1-methylethyl) ester, monohydrochloride (SQ 32,547) | 20 mg |
| Corn starch | 50 mg |
| Gelatin | 7.5 mg |
| Avicel(microcrystalline cellulose) | 25 mg |
| Magnesium stearate | 2.5 mg | were prepared from sufficient bulk quantities by mixing the (R)-3,6-dihydro-4-methyl-2-thioxo-6-[2-(trifluoromethyl)phenyl]-1,5(2H)-pyrimidine-dicarboxylic acid, 1-[1-[(4-fluorophenyl)methyl]-4-piperidinyl]5-(1-methylethyl) ester, monohydrochloride and cornstarch with an aqueous solution of the gelatin. The mixture was dried and ground to a fine powder. The Avicel and then the magnesium stearate were admixed with granulation. This mixture was then compressed in a tablet press to form 1000 tablets each containing 20 mg of active ingredient.

A similar procedure can be employed to form tablets containing 20 mg of active ingredient.

The so-formed tablets may be used for preventing or treating anxiety.

EXAMPLE 8

A tablet formulation for use in treating or preventing anxiety is prepared using the procedure as described in Example 7 except SQ 32,926 is used as the calcium channel blocker.

SQ 32,926 was prepared as follows.

(R)-1-(Aminocarbonyl)-4-(3-chlorophenyl)-1,2,3,4-tetrahydro-6-methyl-2-oxo-5-pyrimidinecarboxylic acid, 1-methylethyl ester (SQ 32,926)

A. 1,4-Dihydro-4-(3-chlorophenyl)-2-methoxy-6-methyl-5-pyrimidinecarboxylic acid, 1-methylethyl ester, oxalate salt A mixture of 3-chlorobenzaldehyde (49.20 g, 350 mmol), isopropyl acetoacetate (50.46 g, 350 mmol), magnesium sulfate (52.5 g), acetic acid (3.5 mL), and piperidine (7.0 mL) in dichloromethane (350 mL) in a 2l three-necked flask under argon was mechanically stirred at room temperature for 20 hours. The reaction was filtered, the filter cake was rinsed heavily with dichloromethane (filtrate volume 1.2l), and the filtrate was washed with 1N sodium hydroxide (75 mL), 1N hydrochloric acid (100 mL), 10% sodium bisulfite (200 mL), saturated sodium chloride (100 mL), dried (magnesium sulfate), and evaporated to give crude Knovenagel product as a yellow foam (96.0 g).

The crude Knovenagel product (~350 mmol) was taken up in dimethylformamide (175 mL) in a 2l three-necked flask under argon, treated with sodium bicarbonate (88.21 g, 1.05 mol), and then treated portionwise with O-methylisourea hydrogen sulfate (78.33 g, 455 mmol) over the next 1 hour. The reaction was then heated at 75° C. (oil bath) overnight under argon. The reaction was cooled, diluted with chloroform (875 mL), filtered (filter cake rinsed thoroughly with chloroform), and evaporated. The thick oily residue was distilled in vacuo at 50° C. (oil bath) to remove most of the dimethylformamide. The resulting residue was taken up in ethyl acetate (1.5l) and washed with water (5×250 mL), saturated sodium chloride (2×250 mL), dried (magnesium sulfate), and evaporated to give a light yellow oil (127.5 g). This oil was dissolved in dichloromethane (175 mL), diluted with isopropanol, and evaporated until only isopropanol remained (final volume about 175 mL). This solution was then treated with a solution of oxalic acid (31.51 g, 350 mmol) in isopropanol (175 mL) and the resulting solid was filtered to give the title compound (69.76 g), melting point 131°-133° C.

B. 1,2,3,4-Tetrahydro-4-(3-chlorophenyl)-6-methyl-3-[[(4-nitrophenyl)oxy]carbonyl]-5-pyrimidinecarboxylic acid, 1-methylethyl ester 1,4-Dihydro-4-(3-chlorophenyl)-2-methoxy-6-methyl-5-pyrimidinecarboxylic acid, 1-methylethyl ester, oxalate salt (68.75 g, 166.5 mmol) was partitioned between chloroform (1l) and 10% sodium carbonate solution (240 mL), shaken thoroughly, and the layers separated. The aqueous phase was reextracted with chloroform (2×300 mL). The combined organic phases were dried (magnesium sulfate) and evaporated to give the free base as a yellow oil.

This free base was transferred (chloroform, 330 mL) to a 2l 3-necked flask fitted with a mechanical stirrer and flushed with argon. The solution was treated with sodium bicarbonate (84.0 g, 1.00 mol) and then treated portionwise over the next 1.5 hours with 4-nitrophenylchloroformate (40.31 g, 200 mmol). After stirring at room temperature overnight, the reaction was filtered through a pad of Celite and evaporated to give a yellow foam. The foamy residue was taken up in a tetrahydrofuran (666 mL) and treated with 3N hydrochloric acid (67 mL, 200 mmol). After stirring for 0.5 hours, the reaction was partially evaporated. The residue was partitioned between ethyl acetate (1.6l) and water 100 mL). The (, organic phase was washed with 10% sodium carbonate (3×100 mL portions), saturated sodium chloride (2×100 mL), dried (magnesium sulfate), and evaporated. The residue was taken up in dichloromethane, diluted with methanol (about 700 mL), and partially evaporated to give the title compound (53.14 g), melting point 165°-167° C. A second crop (8.91 g) precipitated from the partially concentrated mother liquor. The two crops were again taken up in dichloromethane, diluted with methanol, and partially evaporated to give the title compound as colorless crystals (56.35 g), melting point 167°-168° C.

C. (R)-4-(3-Chlorophenyl)-1,2,3,4-tetra-hydro-6-methyl-2-oxo 1-[[(1-pheynlethyl)-amino]carbonyl]-5-pyrimidinecarboxylic acid, 1-methylethyl ester A mixture of 1,2,3,4-tetrahydro-4-(3-chlorophenyl)-6-methyl-3-[[(4-nitrophenyl)oxy]carbonyl]-pyrimidinecarboxylic acid, 1-methylethyl ester (56.00 g, 118 mmol) in acetonitrile (472 mL) under argon was treated with S-(-)-α-methylbenzyl amine (16.76 mL, 130 mmol). After stirring for 0.75 hours, the reaction was evaporated. The residue was taken up in ethyl acetate and washed with 1N sodium hydroxide (4×200 mL), saturated sodium chloride (2×100 mL portions), 10% citric acid (200 mL), saturated sodium chloride (100 mL), dried (magnesium sulfate), and evaporated. The residue was crystallized from isopropyl ether (about 900 mL) to give colorless crystals (21.39 g), melting point 198°-200° C. Recrystallization gave the title compound as colorless crystals (20.13 g), melting point 200°-201° C. $\alpha_D = -273°$ (c=1,chloroform).

D. (R)-1-(Aminocarbonyl)-4-(3-chlorophenyl)-1,2,3,4-tetrahydro-6-methyl-2-oxo-5-pyrimidinecarboxyl acid, 1-methylethyl ester A solution (dissolved upon heating) of (R)-4(3-chlorophenyl)-1,2,3,4-tetrahydro-6-methyl-2-oxo-1-[[( acid, 1-methylethyl ester (18.85 g, 41.34 mmol) in trifluoroacetic acid (40 mL) under argon was heated at 75° C. (oil bath) for 2.0 hours. The reaction was cooled and evaporated. The residue was coevaporated with toluene (twice). The residue was taken up in ethyl acetate (750 mL) and washed with saturated sodium bicarbonate, saturated sodium chloride, dried (magnesium sulfate), and evaporated. The residue was crystallized from isopropyl ether to give colorless crystals (11.15 g), melting point 165°-166° C. A second crop (2.40 g), melting point 163°-165° C, was combined with the first crop (total 13.54 g) and recrystallized from isopropyl ether to give the title compound as colorless crystals (11.45 g), melting point 167°-168° C. $[\alpha]_D = -157°$ (C=1.0, methanol).

Analysis calc'd for $C_{16}H_{18}N_3O_4Cl$: C, 54.62; H, 5.16; N, 11.95; Cl, 10.08. Found: C, 54.49; H, 5.18; N, 11.57; Cl, 10.07.

EXAMPLE 9

Diazepam (as a positive control), and the calcium channel blockers SQ 33,351 (identified in Example 5), SQ 33,537 (identified in Example 6, and diltiazem) were tested for their anti-anxiety effect in the mouse black:white test box employing the following test procedure.

The mouse black:white test box (test of anxiolytic potential using mouse aversion to a brightly lit, white environment)

The studies used naive male albino BKW mice, 25-30 g. Ten mice were normally housed in each cage with free access to food and water. The mice were kept on a 12 hours light-dark cycle with lights off at 10.00 hour.

For assessment of anxiety responding mals were taken in a dark container from a dark holding room to the dimly lit testing room where the experiments were conducted between 13:00 and 18:00 hours. The apparatus used for the detection of changes in anxiety consisted of an open-topped box (45×27×27 cm high) having a smaller portion painted black (40% of area) and illuminated under a dim red light (1×60W) and partitioned from the remainder of the box which was painted white and brightly illuminated with a 60W white light source located 17 cm above the box. The floor area was lined into 9 cm squares. Access between these areas was enabled by means of a 7.5×7.5 cm opening located at floor level in the center of the partition. Animals that had received drug or vehicle injections were placed individually into the center of the white area and their behavior observed over a 5 minute period by remote video recording. An increased exploratory activity (rearings, line crossings) in the brightly-lit environment was taken as an index of anxiolytic action when a dark environment was simultaneously available. Anxiolytic activity was also associated with a delayed latency to move from the white to the black environment and a reduced % of time spent in the black environment. Thus, four behavioral parameters were noted every minute, the number of exploratory rearings in the white and black areas, the number of line crossings in the white and black areas, the latency to move from the white to the black area, and the % of time spent in the black area. Experimenters remained blind to drug treatment throughout, the code only being broken after analysis was complete.

Animals were used on a single occasion only, in experimental groups of 5 (N=5). Vehicle treated controls were run on each day of testing. Testing was carried out both after intraperitoneal (i.p.) and oral (p.o.) dosing. Where time courses of drug action were assessed, fresh groups of animals were used on each test occasion. To determine whether drug effects were maintained on subchronic treatment mice were dosed twice daily (b.d.) for 6 days and then tested 45 to 60 minutes after administration of the last dose (see below). To determine whether anxiogenesis or other adverse effects developed on withdrawal of subchronic treatment mice were treated twice daily with drug for 6 days then assessed in the black:white box 24 hours after drug withdrawal (withdrawal effects, or lack of, were confirmed by testing further groups of mice 48 hours and 96 hours after withdrawal of drug).

Throughout the studies diazepam (Roche) was used as the positive control. Preparation was in minimum PEG made up to volume with distilled water (route i.p., pretreatment 60 minutes); SQ 33,351 (FIG. 2) (route i.p., pretreatment 45 to 60 minutes); SQ 33,537 (FIG. 3) (route i.p., pretreatment 45 to 60 minutes); and diltiazem (FIG. 4) (route i.p., pretreatment 45 to 60 minutes), were prepared in distilled water.

Results

Figure 1:
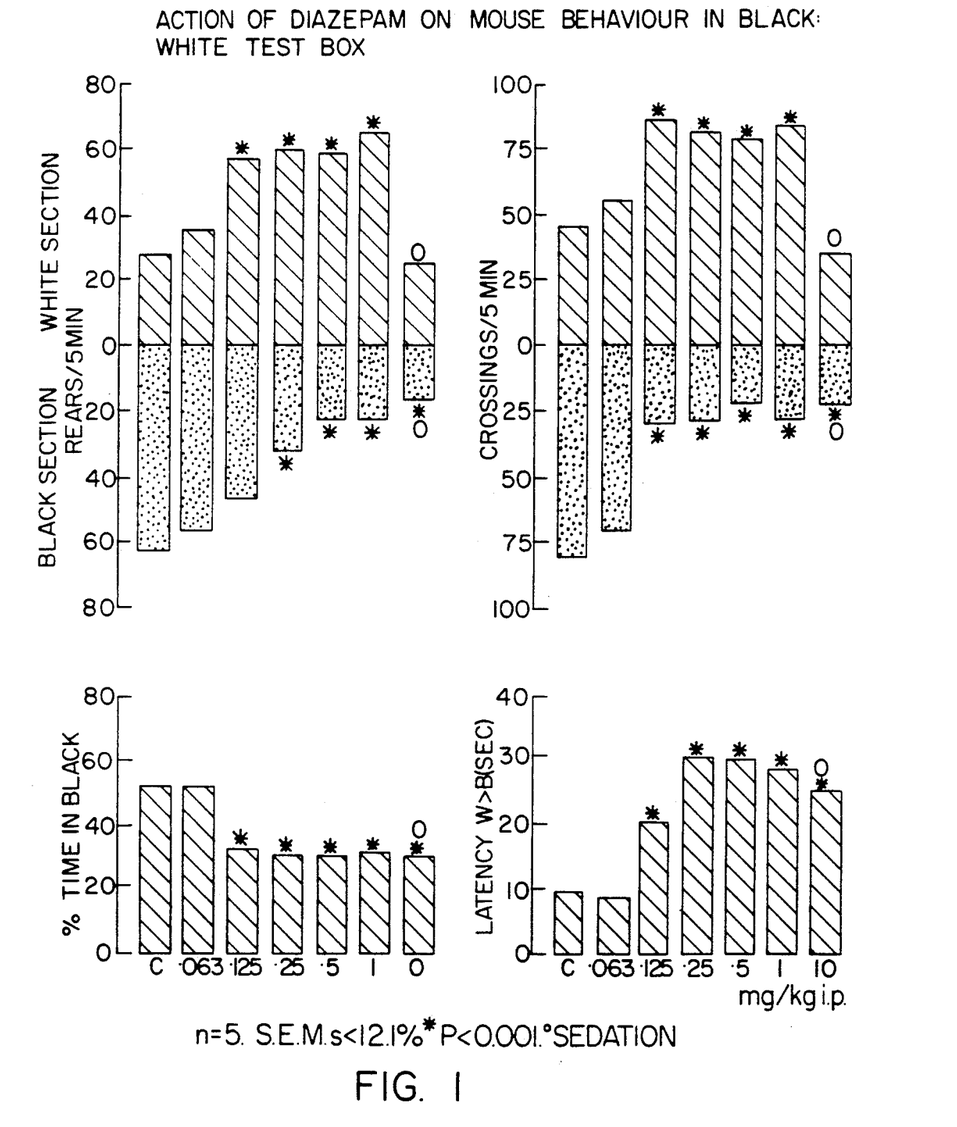
FIG. 1 shows the action of diazepam on mouse behavior in a black:white test box. $n=5$. S.E.M.s shown less than 12.1% *$P<0.001$. 0=sedation.

Diazepam caused changes in mouse responding consistent with an anxiolytic potential at doses of 0.125-1 mg/kg i.p. Sedation developed at 10 mg/kg. The anxiolytic action was characterized by increased exploratory rearings and line crossings in the white section of the test box, with corresponding reductions in the white, reduced % of time spent in the black, and delayed latency to move from the white to the black compartment (FIG. 1).

Figure 2:
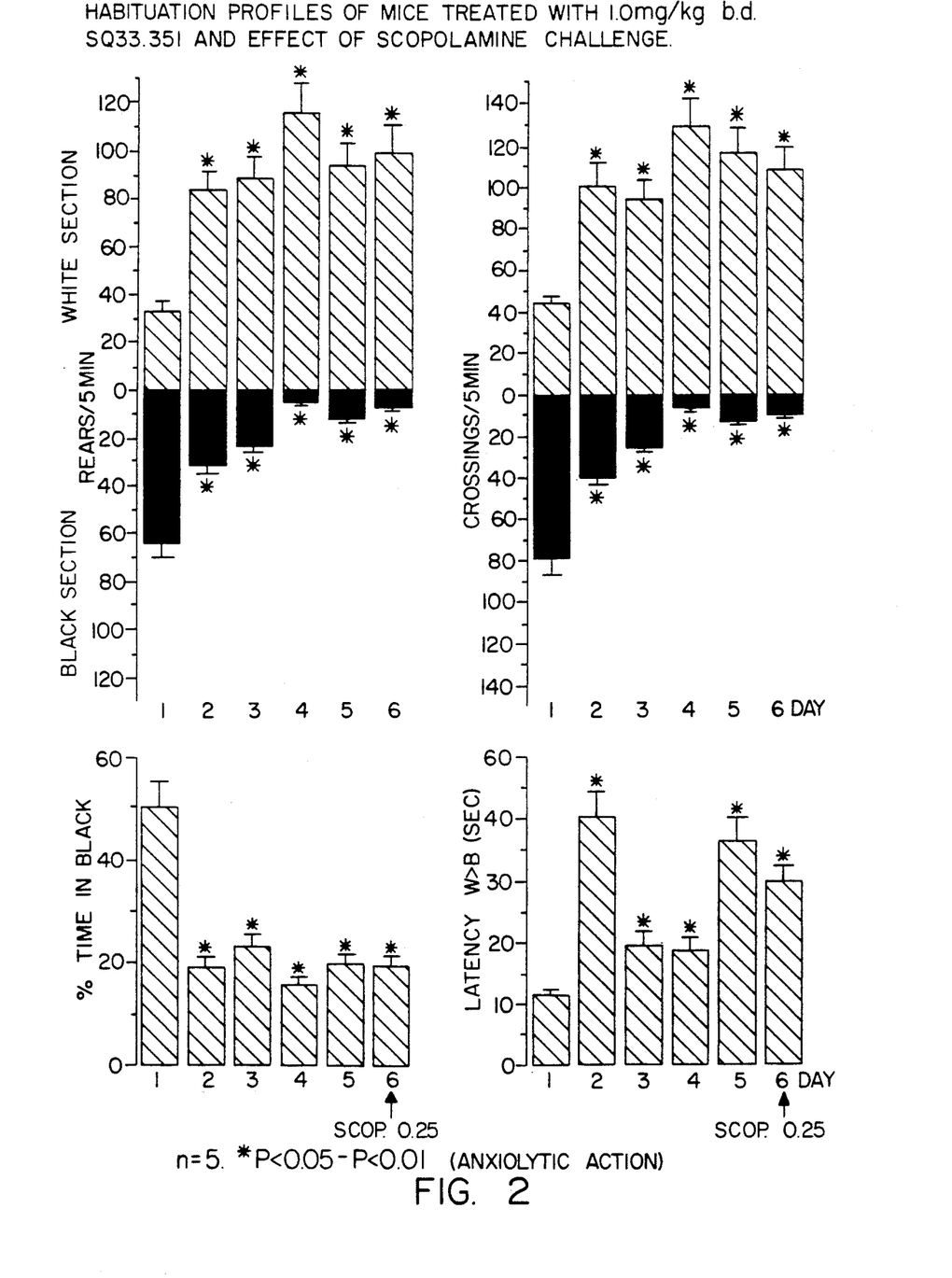
FIG. 2 shows the action of the calcium channel test box. $n=5$. *$P<0.05$-$P<0.01$.
Figure 3:
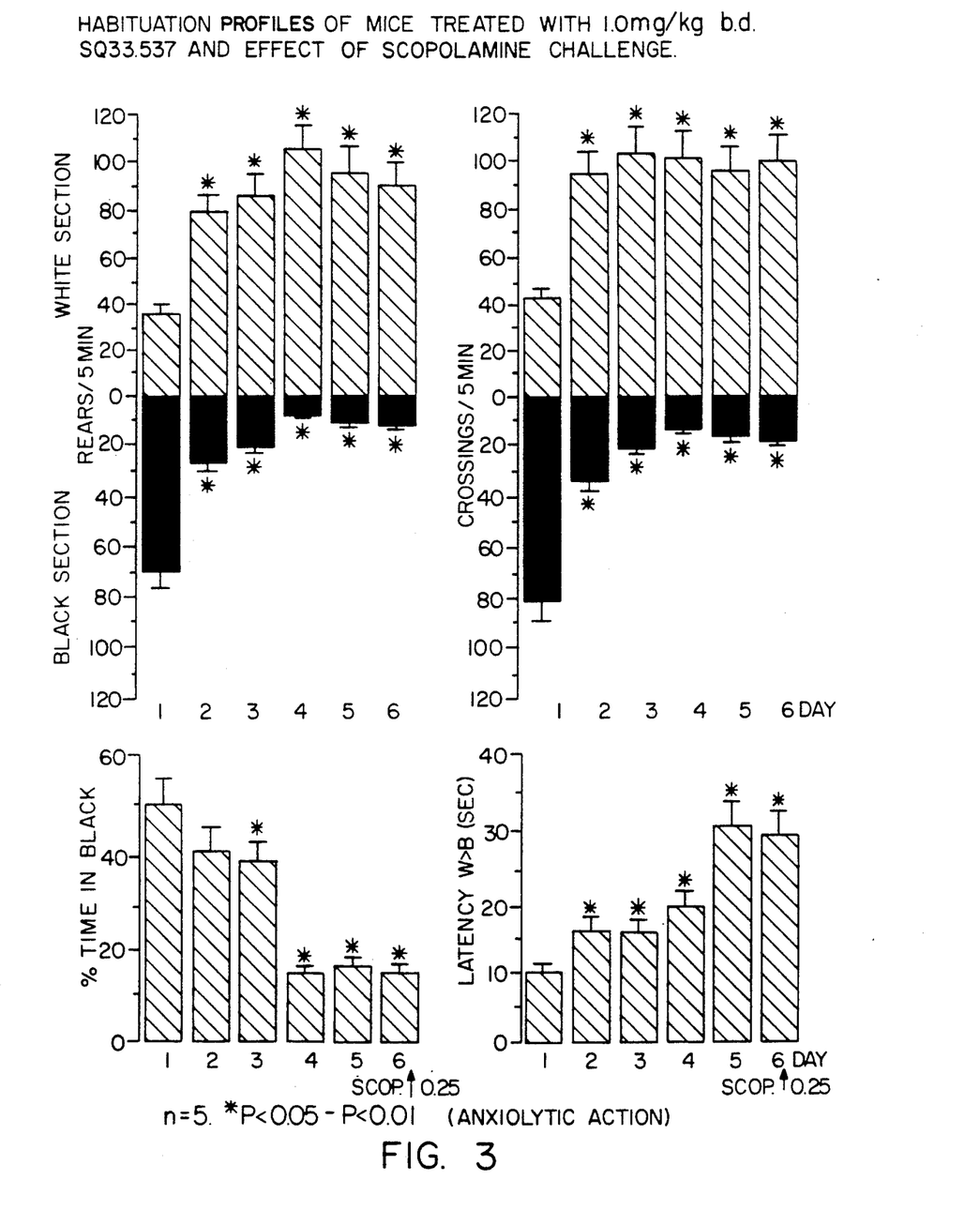
FIG. 3 shows the action of SQ 33,537 on mouse behavior in the black:white test box. $n=5$. *$P<0.05$-$P<0.01$.
Figure 4:
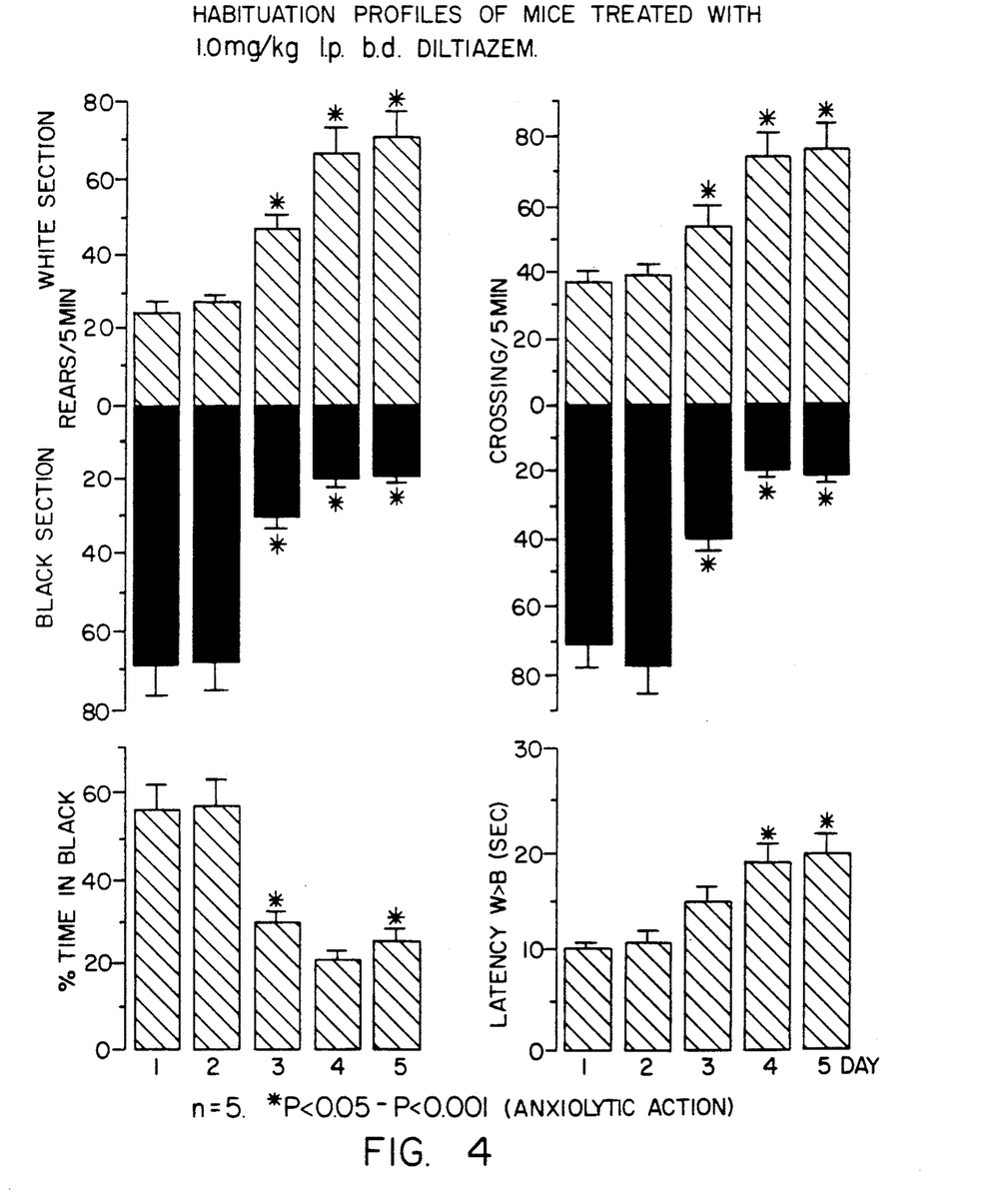
FIG. 4 shows the action of diltiazem on mouse behavior in the black:white test box. $n=5$. *$P<0.05$-$P<0.001$.

SQ 33,351, SQ 33,537 and diltiazem caused a similar change in behavior as recorded for diazepam, that is increased rearings and line crossings in the white, normally averse, envioronment, with corresponding reductions in the black, and reduced % of time spent in the black, and delayed latency to move to the black (FIGS. 2 to 4). The effects of scopolamine on day 6 were masked by the anxiolytic effects of SQ 33,351 and SQ 33,537 (FIGS. 2 and 3 respectively).

The test results shown in FIGS. 2, 3, and 4 show that the calcium channel blocker tested, namely, SQ 33,351, SQ 33,537 and diltiazem had anti-anxiety activity and thus would be useful in reducing anxiety.

What is claimed is:

1. A method for inhibiting onset of or treating anxiety in a mammalian specie, which comprises administering to a mammalian specie in need of such treatment an anxiolytic effective amount of a calcium channel blocker which is diltiazem, a pyrimidine having the formula including a pharmaceutically acceptable salt thereof wherein:

$R_a$ is 2-(trifluoromethyl)phenyl, 2-chlorophenyl, 2-nitrophenyl, or 3-nitrophenyl;

and $R_b$ is phenyl, 2-chlorophenyl, or 4-fluorophenyl or a pyrimidine having the formula or a pharmaceutically acceptable salt thereof wherein

X is oxygen or sulfur;

$R_x$ is hydrogen, alkyl, cycloalkyl, aryl, or arylalkyl and $R_c$ is hydrogen, alkyl, cycloalkyl, aryl, $$-\underset{R_h}{\overset{R_g}{\underset{|}{\overset{|}{C}}}}-(CH_2)_n-Y^b, \quad -\underset{R_h}{\overset{R_g}{\underset{|}{\overset{|}{C}}}}-(CH_2)_p-Y^c$$

or halo substituted alkyl, or $R_x$ and $R_c$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-piperazinyl or 1-pyrrolidinyl, 1-piperidinyl, or 1-azeipinyl substituted with alkyl, alkoxy, alkylthio, halo, trifluoromethyl or hydroxy;

$R_d$ is hydrogen, alkyl, alkenyl, alkynyl, cycloalkyl, aryl, or halo substituted alkyl;

$R_e$ is hydrogen, alkyl, cycloalkyl, aryl, or halo substituted alkyl;

$R_f$ b is 2,1,3-benzoxadiazol-4-yl, phenyl, or phenyl substituted with one, two or three alkyl, halo, nitro, cyano, amino, dialkylamino, trifluoromethyl, isothiocyanato or isocyanato groups;

$R_g$ and $R_h$ are each independently hydrogen, alkyl, $-(CH_2)_{q1}$-aryl or $-(CH_2)_{q1}$-cycloalkyl;

$Y^a$ is cycloalkyl, aryl, hydroxyl, alkoxy, aryl-$(CH_2)_m$—O—, mercapto, alkylthio, aryl-$(CH_2)_m$—S—, amino, substituted amino, carbamoyl, (substituted carboxyl, alkoxycarbonyl, $Y^b$ is cycloalkyl, aryl, carbamoyl, (substituted carboxyl, alkoxycarbonyl, $Y^c$ is hydroxyl, alkoxy, aryl—$(CH_2)_{m1}$—O—, mercapto, alkylthio, aryl—$(CH_2)_{m1}$—S—, alkyl-C—O—, aryl-$(CH_2)_{m1}$—C—O—, amino, or substituted amino;

$q_1$ is 0, 1, 2 or 3;

$m_1$ is 0 or an integer of 1 to 6;

$n_1$ is 0 or an integer of 1 to 5; and

$p_1$ is an integer of 1 to 5; wherein the term "cycloalkyl" refers to a cycloalkyl group having 3,4,5,6 or 7 carbon atoms;

the term "aryl" refers to phenyl or phenyl substituted with one, two or three alkyl, alkoxy, alkylthio, halo, nitro, cyano, hydroxy, amino, alkylamino, dialkylamino, trifluoromethyl, isothiocyanato, isocyanato, or difluoromethyoxy groups;

the term "substituted amino" refers to a group of the formula —$NZ_1Z_2$ wherein $A_1$ is hydrogen, alkyl, or aryl—$(CH_2)_{m1}$—and $Z_2$ is alkyl or aryl—$(CH_2)_{m1}$— or a 4-phenyl-1,4-dihydropyridine having the formula structure wherein $R_1$ and $R_2$ may be the same or different and are lower alkyl or lower alkoxy (lower alkyl) where lower alkyl and lower alkoxy contain 1 to 4 carbons.

2. The method as defined in claim 1 wherein said calcium channel blocker is administered in single or divided doses of from about 1 to about 300 mg/1 to 4 times daily.

3. The method as defined in claim 1 wherein the calcium channel blocker is diltiazem.

4. The method as defined in claim 1 whrein the calcium channel blocker is of the pyrimidine type.

5. The method as defined in claim 1 wherein the pyrimidine is (R)-3,6-dihydro-4-methyl-2-thioxo-6-[2-(trifluoromethyl)phenyl]-1,5(2H)-pyrimidinedicarboxylic acid, 1-[1-[(4-fluorophenyl)-methyl]-4-piperidinyl]-5-(1-methylethyl) ester, monohydrochloride.

6. The method as defined in claim 1 wherein the calcium channel blocker has the name (R)-1-(aminocarbonyl)-4-(3-chlorophenyl)-1,2,3,4-tetrahydro-6-methyl-2-oxo-5-pyrimidinecarboxylic acid, 1-methylethyl ester.

7. The method as defined in claim 1 wherein the calcium channel blocker is a 4-pheynl-1,4-dihydropyridine.

8. The method as defined in claim 1 wherein a calcium chanel blocker is administered orally or parenterally.

9. The method as defined in claim 1 wherein a calcium channel blocker is admixed with a pharmaceutically acceptable carrier thereofor.

10. The method as defined in claim 1 wherein the calcium channel blocker is diltiazem, or a 4-phenyl-1,4-dihydropyridine.

11. The method as defined in claim 10 wherein the 4-phenyl-1,4-dihydropyridine is nifedipine or nitrendipine.

12. A method for inhibiting onset of or treating anxiety in a mammalian specie associated with withdrawal from drugs of dependency and/or addiction, which comprises administering to a mammalian specie in need of such treatment an anxiolytic effective amount of a calcium channel blocker which is diltiazem, a pyrimidine having the formula including a pharmaceutically acceptable salt thereof wherein:

$R_a$ is 2-(trifluoromethyl)phenyl, 2-chlorophenyl, 2-nitrophenyl, or 3-nitrophenyl;

and $R_b$ is phenyl, 2-chlorophenyl, or 4-fluorophenyl or a pyrimidine having the formula or a pharmaceutically acceptable salt thereof wherein

X is oxygen or sulfur;

$R_x$ is hydrogen, alkyl, cycloalkyl, aryl, or arylalkyl and $R_c$ is hydrogen, alkyl, cycloalkyl, aryl, or halo substituted alkyl, or $R_x$ and $R_c$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-piperazinyl or 1-pyrrolidinyl, 1-piperidinyl, or 1-azeipinyl substituted with alkyl, alkoxy, alkylthio, halo, trifluoromethyl or hydroxy;

$R_d$ is hydrogen, alkyl, alkenyl, alkynyl, cycloalkyl, aryl, or halo substituted alkyl;

$R_e$ is hydrogen, alkyl, cycloalkyl, aryl, or halo substituted alkyl;

$R_f$ b is 2,1,3-benzoxadiazol-4-yl, phenyl, or phenyl substituted with one, two or three alkyl, halo, nitro, cyano, amino, dialkylamino, trifluoromethyl, isothiocyanato or isocyanato groups;

$R_g$ and $R_h$ are each independently hydrogen, alkyl, —$(CH_2)_{q1}$-aryl or —$(CH_2)_{q1}$-cycloalkyl;

$Y^a$ is cycloalkyl, aryl, hydroxyl, alkoxy, aryl-$(CH_2)_m$—O—, mercapto, alkylthio, aryl-$(CH_2)_m$—S—, amino, substituted amino, carbamoyl, (substituted carboxyl, alkoxycarbonyl,

$Y^b$ is cycloalkyl, aryl, carbamoyl, (substituted carboxyl, alkoxycarbonyl, $Y^c$ is hydroxyl, alkoxy, aryl—$(CH_2)_{m1}$—O—, mercapto, alkylthio, aryl—$(CH_2)_{m1}$—S—, amino, or substituted amino;

$q_1$ is 0, 1, 2 or 3;

$m_1$ is 0 or an integer of 1 to 6;

$n_1$ is 0 or an integer of 1 to 5; and $p_1$ is an integer of 1 to 5; wherein the term "cycloalkyl" refers to a cycloalkyl group having 3,4,5,6 or 7 carbon atoms.

the term "aryl" refers to phenyl or phenyl substituted with one, two or three alkyl, alkoxy, alkylthio, halo, nitro, cyano, hydroxy, amino, alkylamino, dialkylamino, trifluoromethyl, isothiocyanato, isocyanato, or difluoromethyoxy groups;

the term "substituted amino" refers to a group of the formula —$NZ_1Z_2$ wherein $A_1$ is hydrogen, alkyl, or aryl—$(CH_2)_{m1}$—and $Z_2$ is alkyl or aryl—$(CH_2)_{m1}$— or a 4-phenyl-1,4-dihydropyridine having the formula structure wherein $R_1$ and $R_2$ may be the same or different and are lower alkyl or lower alkoxy (lower alkyl) where lower alkyl and lower alkoxy contain 1 to 4 carbons.

13. The method as defined in claim 12 for reducing anxiety associated with nicotine withdrawal, alcohol withdrawal, diazepam withdrawal or cocaine withdrawal.

14. The method as defined in claim 12 for reducing anxiety and thus facilitating withdrawal from nicotine, alcohol, diazepam or cocaine.

15. The method as defined in claim 12 for reducing anxiety associated with nicotine withdrawal.

16. The method as defined in claim 12 for reducing anxiety associated with alcohol withdrawal.

17. The method as defined in claim 1 wherein a calcium channel blocker is administered in the form of tablets, capsules or by injection.

18. The method as defined in claim 1 wherein said calcium channel blocker is diltiazem, (R)-3,6-dihydro-4-methyl-2-thioxo-6-[2-(trifluoromethyl)phenyl]-1,5(2H)-pyrimidinedicarboxylic acid, 1-[1-[(4-fluorophenyl)-methyl]-4-piperidinyl]-5-(1-methylethyl) ester, monohydrochloride (SQ 32,547) or (R)-1-(aminocarbonyl)-4-(3-chlorophenyl)-1,2,3,4-tetrahydro-6-methyl-2-oxo-5-pyrimidinecarboxylic acid, 1-methylethyl ester (SQ 32,926) and is administered systemically in an amount of from about 0.1 to about 500 ml/l to 4 times a day.

19. A method for inhibiting onset of or treating anxiety in a mammalian specie, which comprises administering to a mammalian specie in need of such treatment an anxiolytic effective amount of a calcium channel blocker which is verapamil.

20. A method for inhibiting onset of or treating anxiety in a mammalian specie associated with withdrawal from drugs of dependency and/or addiction, which comprises administering to a mammalian specie in need of such treatment an anxiolytic effective amount of a calcium channel blocker which is verapamil.

* * * * *